(12) United States Patent
Kopesky et al.

(10) Patent No.: US 8,637,063 B2
(45) Date of Patent: Jan. 28, 2014

(54) HYDROLYZED HYDROGELS

(75) Inventors: Edward T. Kopesky, Arlington, MA (US); Jason Berlin, Everett, MA (US); Martin F. Van Buren, Chelmsford, MA (US); Gavin J. C. Braithwaite, Cambridge, MA (US)

(73) Assignee: Cambridge Polymer Group, Inc., Boston, MA (US)

( * ) Notice: Subject to any disclaimer, the term of this patent is extended or adjusted under 35 U.S.C. 154(b) by 0 days.

(21) Appl. No.: 13/132,507

(22) PCT Filed: Dec. 7, 2009

(86) PCT No.: PCT/US2009/066958
§ 371 (c)(1),
(2), (4) Date: Jun. 29, 2011

(87) PCT Pub. No.: WO2010/065951
PCT Pub. Date: Jun. 10, 2010

(65) Prior Publication Data
US 2011/0256201 A1    Oct. 20, 2011

Related U.S. Application Data

(60) Provisional application No. 61/193,536, filed on Dec. 5, 2008.

(51) Int. Cl.
*A61F 13/00* (2006.01)
*A61K 31/74* (2006.01)
*A61F 2/02* (2006.01)
*A61F 2/28* (2006.01)

(52) U.S. Cl.
USPC ..... 424/422; 424/78.08; 524/916; 623/11.11; 623/16.11; 623/23.58

(58) Field of Classification Search
None
See application file for complete search history.

(56) References Cited

U.S. PATENT DOCUMENTS

| | | | | |
|---|---|---|---|---|
| 3,408,429 A | * | 10/1968 | Wichterle | 264/2.1 |
| 3,875,302 A | | 4/1975 | Inoue | |
| 4,104,208 A | * | 8/1978 | Kido et al. | 521/53 |
| 4,224,262 A | | 9/1980 | Baird, Jr. et al. | |
| 4,314,032 A | | 2/1982 | Murayama et al. | |
| 4,385,155 A | | 5/1983 | Michaels | |
| 4,978,713 A | * | 12/1990 | Goldenberg | 525/61 |

(Continued)

FOREIGN PATENT DOCUMENTS

WO    2008/131451    10/2008

OTHER PUBLICATIONS

International Preliminary Report on Patentability from corresponding PCT Appln. No. PCT/US2009/066958 dated Jun. 7, 2011.

(Continued)

*Primary Examiner* — Carlos Azpuru
*Assistant Examiner* — Casey Hagopian
(74) *Attorney, Agent, or Firm* — Grossman, Tucker, Perreault & Pfleger, PLLC

(57) ABSTRACT

The invention provides methods of making hydrolyzed cross-linked polyvinyl alcohol (PVA) hydrogels by polymerizing vinyl acetate (VAc) monomers to polyvinyl acetate (PVAc) polymer network by chemical-crosslinking and hydrolysis. The invention also provides methods for including pendant chains in the hydrogel during the polymerization process. Materials produced and use of the cross-linked hydrolyzed PVA hydrogels also are disclosed herein.

18 Claims, 10 Drawing Sheets

R = monomers or polymers

(56) References Cited

U.S. PATENT DOCUMENTS

| | | | |
|---|---|---|---|
| 5,210,111 | A | 5/1993 | Goldenberg et al. |
| 5,779,943 | A * | 7/1998 | Enns et al. .................. 264/1.7 |
| 5,981,826 | A | 11/1999 | Ku et al. |
| 6,231,605 | B1 | 5/2001 | Ku |
| 7,235,592 | B2 | 6/2007 | Muratoglu et al. |
| 7,282,165 | B2 | 10/2007 | Williams, III et al. |
| 7,619,009 | B2 | 11/2009 | Ruberti et al. |
| 2003/0004279 | A1 * | 1/2003 | Kowaka et al. ............ 525/330.6 |
| 2004/0092653 | A1 | 5/2004 | Ruberti et al. |
| 2004/0171740 | A1 | 9/2004 | Ruberti et al. |
| 2006/0237880 | A1 | 10/2006 | Wicker et al. |
| 2008/0208347 | A1 | 8/2008 | Muratoglu et al. |
| 2008/0274161 | A1 | 11/2008 | Muratoglu et al. |

OTHER PUBLICATIONS

Bodugoz-Senturk et al., "The effect of polyethylene glycol on the stability of pores in polyvinyl alcohol hydrogels during annealing", Science Direct, Biomaterials, vol. 29, 2008, Boston, MA, pp. 141-149.

Bourke et al., "A Photo-Crosslinked Poly(vinyl Alcohol) Hydrogel Growth Factor Release Vehicle for Wound Healing Applications", AAPS PharmSci 2003; 5 (4) Article 33, Piscataway, NJ, pp. 1-11.

Cauich-Rodriguez et al., Summary of: "Physiochemical characterization of hydrogels based on polyvinyl alcohol-vinyl acetate blends", Journal of Applied Polymer Science, 82, Issue 14, 2001, pp. 3578-3590.

Covert et al., "Friction characteristics of a potential articular cartilage biomaterial", Science Direct, Wear 255, 2003, Atlanta, GA, pp. 1064-1068.

Guo et al., Abstract of: Synthesis of biocompatible polymeric hydrogels with tunable adhesion to both hydrophobic and hydrophilic surfaces, Biomacromolecules, vol. 6, 2008, Shanghai, China, pp. 1637-1642.

Hassan et al., "Structure and Applications of Poly(vinyl alcohol) Hydrogels Produced by Conventional Crosslinking or by Freezing/Thawing Methods", Advances in Polymer Science, vol. 153, 2000, West Lafayette, IN, pp. 37-65.

Hong et al., "Effects of Mixed Solvent on Gelation of Poly(vinyl alcohol) Solutions", 1999, Taipei, Taiwan, pp. 1113-1120.

Horkay et al., Summary of: "Small Angle Neutron Scattering in Poly(vinyl alcohol) Hydrogels", Macromolecules, 1994, vol. 27 (7), pp. 1795-1798.

Horkay et al., Summary of: "Poly(vinyl alcohol-vinyl acetate) copolymer hydrogels: scattering and osmotic observations", Macromolecules, 1993, vol. 26 (13), pp. 3375-3380.

McNickle et al., "Overview of Existing Cartilage Repair Technology", Sports Med Arthrosc Rev, vol. 16, No. 4, 2008, Chicago, IL, pp. 196-201.

Murakami et al., Preparation of Micron-Sized Poly(vinyl acetate) Particles by Suspension Polymerization Using Poly (vinyl alcohol)-Borate Complex Stabilizer, Polymer Journal, vol. 25, No. 2, 1993, Kumamoto, Japan, pp. 205-207.

Ohsedo et al., "Surface Friction of Hydrogels with Well-Defined Polyelectrolyte Brushes", American Chemical Society, vol. 20, 2004, Sapporo, Japan, pp. 6549-6555.

Ranjha, "Swelling Behaviour of pH-Sensitive Crosslinked Poly(Vinyl Acetate Co-Acrylic Acid) Hydrogels for Site Specific Drug Delivery", Pakistan Journal of Pharmaceutical Sciences, vol. 12, No. 1, 1999, Multan, Pakistan, pp. 33-41.

Vanderhooft et al., Abstract of: "Synthesis and Characterization of Novel Thiol-Reactive Poly(ethylene glycol) Cross-Linkers for Extracellular-Matrix-Mimetic Biomaterials", Biomacromolecules, vol. 8 (9), 2007, Salt Lake City, UT, pp. 2883-2889.

Velazco-Diaz et al., Abstract of: "Synthesis and Characterization of Hydrogels Based on Poly(vinyl alcohol)-g-Poly (styrene) Copolymers", Ind. Eng. Chem. Res., vol. 44 (18), 2005, Coyoacan, Mexico, pp. 7092-7097.

Xiao et al., "Controlled preparation of physical cross-linked starch-g-PVA hydrogel", Carbohydrate Polymers, vol. 64, Issue 1, 2006, Quanzhou, China, pp. 37-40.

\* cited by examiner

HYDROLYZED HYDROGELS

CROSS-REFERENCE TO RELATED APPLICATIONS

This application is the U.S. National Phase Application under 35 U.S.C. §371 of International Patent Application No. PCT/US2009/066958 filed Dec. 7, 2009, which claims the benefit of U.S. Provisional Patent Application No. 61/193,536 filed on Dec. 5, 2008, the teachings of both of which are incorporated herein by reference.

FIELD OF THE INVENTION

The invention relates to methods of making hydrolyzed cross-linked poly(vinyl alcohol) (PVA) hydrogels by polymerizing vinyl acetate (VAc) monomers to poly(vinyl acetate) (PVAc) polymer network by chemical-crosslinking and hydrolysis. The invention also relates to methods for incorporating pendant chains in the hydrogel during the polymerization process. The invention further relates to the materials produced and use of the cross-linked hydrolyzed PVA hydrogels. Other aspects and advantages of the invention are disclosed herein.

BACKGROUND OF THE INVENTION

Poly(vinyl alcohol) (PVA) is known to form excellent biocompatible hydrogels. Currently available methods of making poly(vinyl alcohol) (PVA)-based materials have focused on hydrogels prepared using freeze-thawing techniques (see Ku, D. N. Poly(vinyl alcohol) hydrogel. U.S. Pat. No. 6,231,605; Ku, D. N.; Braddon, L. G.; Wootton, D. M. Poly(vinyl alcohol) cryogel. U.S. Pat. No. 5,981,826; and Inoue, T. Gelled vinyl alcohol polymers and articles therefrom. U.S. Pat. No. 3,875,302).

The scientific literature also has focused largely on the properties of freeze-thawed PVA hydrogels (see Hassan, C. M., Peppas, N. A. *Advances in Polymer Science* 2000, 153, 37-65). Other studies have investigated PVA hydrogels prepared using mixed solvents (see Hong, P.-D., Chou, C.-M., Chuang, W.-T. *Journal of Applied Polymer Science* 2001, 79, 1113-1120; Bodugoz-Senturk, H., Choi, J., Oral, E.; Kung, J. H., Macias, C. E., Braithwaite, G., Muratoglu, O. K. *Biomaterials* 2008, 29, (2), 141-149; US Publication Nos. US 2004-0092653; US 2004-0171740; US 2006-020781; US 2007-0054990; US 2007-016754; US 2008-0274161; and US 2008-0208347). Both freeze-thawed and mixed solvent hydrogels contain only physical crosslinks comprised of PVA crystallites. No chemical crosslinkers are used.

Chemically crosslinked PVA hydrogels have been reported. PVA beads crosslinked with aldehydes for use as a water-loss agent in oil drilling fluids have been developed (Michaels, A. S. Method of Preparing Crosslinked Poly(vinyl alcohol). U.S. Pat. No. 4,385,155). PVA beads crosslinked with cyclic crosslinking agents for use in gel chromatography also have been developed (Murayama, N., Sakagami, T. Crosslinked Polyvinyl Alcohol Gel. U.S. Pat. No. 4,314,032).

Some approaches combined chemical and physical crosslinking. In the work of Williams et al., a solution of PVA in a mixture of DMSO and water is freeze-thawed, subsequently gamma-irradiated, and then the surface is crosslinked with boric acid (Williams, P. F., Ngo, C., DeMaria, C. Wear Resistant Hydrogel For Bearing Application. 7282165, 2007). Another approach is described in Muratoglu et al., U.S. Pat. No. 7,235,592). Recently, Muratoglu et al. have published WO 2008/131251.

PVA and copolymers of PVA are known (see for example Cauich-Rodriguez et al. *J Appl Polym Sci* 82 (14) 3578-3590; Horkay macromolecules 1993 (26) 3375); and chemically crosslinked PVA hydrogels are also known (Bourke S L, Al-Khalili M, Briggs T, Michniak B B, Kohn J, Poole-Warren L A. A Photo-Crosslinked Poly(vinyl Alcohol) Hydrogel Growth Factor Release Vehicle for Wound Healing Applications. *AAPS PharmSci.* 2003; 5 (4)). There has been much discussion of PVA based hydrogels (Hassan *Advances in Polymer Science* 2000) and their blends and IPNs resulting from these materials.

Attachment of an active molecule to a hydrogel is known (See B. Ratner et al. "Biomaterials Science (Second Edition)" (2004)). A mono-functional PEG molecule can be coupled on one end to a therapeutic. For example, a mono-functional PEG molecule can be coupled on one end of a protein or an amino acid conjugate, while the other end contains an acrylate group. This molecule could act both as the mono-functional PEG component and a sustained drug release agent.

Crosslinkers

Various crosslinkers have been disclosed in the literature for crosslinking polymers, e.g. novel thiol PEG crosslinkers (Vanderhooft biomacromolecules 2007 8(9) 2883) as well as EGDMA crosslinkers used with VAc, acrylic acid and methacrylic acid (Ranjha *Pakistan Journal of Pharmaceutical Sciences* 1999 12(1) 33-41). Hydrogels also have been formed by partially hydrolyzed PVAc where the crosslinking occurred between the hydroxyl groups and hydrolysis level controlled the adhesion to tissue (Guo biomacromolecules 2008 9(6) 1637). PVA has been shown to crosslink using glutaraldehyde (*Horkay macromolecules* 1994 27 1795), acrylamide groups (*Martens Chemistry of Matter* 2007 19(10) 2641. In the patent literature PVA has been crosslinked using polyoxirane (U.S. Pat. No. 4,598,122, Polyoxirane crosslinked polyvinyl alcohol hydrogel contact lens).

Surface Friction

A number of authors have discussed surface friction of hydrogels, and the weaknesses of existing materials relative to cartilage (R. J. Covert, R. D. Ott, D. N. Ku, Friction characteristics of a potential articular cartilage biomaterial. *Wear* 255 (2003) and A. G. McNickle, M. T. Provencher, B. J. Cole, Overview of Existing Cartilage Repair Technology. *Sports Med Arthrosc Rev* 16(4), 196-201(2008)).

Hydrolysis of PVAc to PVA Hydrogels

PVA microspheres can be manufactured by crosslinking VAc in emulsion polymerization, and then hydrolyzing the subsequent PVAc-base "organogel". See for example, Ryoichi Murakami, Hiroshi Hachisako, Kimiho Yamada and Yoshiaki Motozato, *Polym. J.,* 25, 205 (1993), which describes the preparation of PVA microspheres by creating PVAc microspheres then hydrolyzing using methanol in an aqueous solution of sodium sulfate. Another method for making particles describes a crosslinked polyvinyl alcohol gel obtained by copolymerizing vinyl acetate and a crosslinking agent and hydrolyzing the product (Murayama and Sakagami, U.S. Pat. No. 4,314,032, Crosslinked polyvinyl alcohol gel). However, this is not the only way to make PVA microspheres, as David Lee Wise (2000) "*Handbook of pharmaceutical controlled release technology*" points out. In addition, the idea of using VAc and then hydrolyzing has been disclosed as part of a copolymer (Xiao, *Carbohydrate polymers* 64(1) 37-40 and Velazco-Diaz, *Industrial Engineering and Chemical Research* 2005 44(18) 7092-7097, Ranjha, *Pakistan Journal of Pharmaceutical Sciences* 1999 12(1) 33-41). Baird et al. (U.S. Pat. No. 4,224,262 Crosslinked copolymer of an olefin and vinyl alcohol) described a crosslinked hydrogel formed by using a copolymer of an olefin and vinyl ester and crosslinking using irradiation with subsequent hydrolysis.

Hydrogels having physical crosslinks (thetagels) prepared without chemical crosslinkers, irradiation and thermal cycling are disclosed in U.S. Pat. Nos. 7,619,009 and 7,485,670.

Pendant Chains

Pendant chains with specific functionality have been discussed in the context of allowing crosslinking (*Martens Chemistry of Matter* 2007 19(10) 2641) and (U.S. Pat. No. 5,210,111-Crosslinked hydrogels derived from hydrophilic polymer backbones) which discusses generating a PVA backbone and pendant side-groups, although points out the complexity of the chemistry involved. This PVA backbone could be formed in to a hydrogel using conventional PVA crosslinkers, such as glutaraldehyde as described above. The target application for this patent is contact lenses. Pendant side groups have been known to be used to modify surface friction in hydrogels, see for example Ohsedo, et al. "Surface Friction of Hydrogels with Well-Defined Polyelectrolyte Brushes" *Langmuir* 2004 20(16), 6549-6555.

General Hydrogel Implantables

The idea of a multi-functionality hydrogel that is composed of alcohol groups amongst others, and is implantable, has been disclosed, for example, Thomas U.S. application Ser. No. 11/969,591, CHEMICAL COMPOSITION OF HYDROGELS FOR USE AS ARTICULATING SURFACES). U.S. application Ser. No. 11/833,549, Multi-polymer Hydrogels, discusses generating IPN structures for implantation. In addition, degradable hydrogels have been shown to form from PVA chains with polymerizable pendant groups. (U.S. Pat. No. 6,710,126 Degradeable poly(vinyl alcohol) Hydrogels).

SUMMARY OF THE INVENTION

The present invention relates to methods of making hydrolyzed cross-linked hydrogels such as (PVA)-hydrogels. The invention also relates to hydrogels produced by the methods described herein.

One aspect of the invention provides methods of making hydrogels comprising the steps of: a) polymerizing a monomer in the presence of a crosslinking agent, thereby producing a crosslinked polymer network; and b) hydrolyzing the crosslinked polymer network by any suitable method to form a hydrogel having hydrophilic polymer network.

In another aspect, the invention provides methods of making a hydrolyzed cross-linked poly(vinyl alcohol) (PVA)-hydrogels, wherein the method comprises the steps of: a) polymerizing vinyl acetate (VAc) monomers by chemical-crosslinking, thereby producing a poly(vinyl acetate) (PVAc) polymer network; and b) hydrolyzing the crosslinked PVAc polymer network, thereby forming a hydrolyzed PVA hydrogel.

Products obtainable by the methods are an aspect of the invention and are provided herein.

According an embodiment of the invention, the crosslinking agent has two or more end groups comprised of methacrylate groups, wherein the methacrylate group comprises acrylate or any group having two double bonds that can be compatible with the vinyl acetate.

According another embodiment of the invention, the crosslinking agent can be glutaraldehyde, epichlorohydrin, ethyleneglycol dimethacrylate (EG-DMA), diallyl succinate, polyethylene glycol divinyl ether, butanediol diacrylate, dimethacrylate with one or more ethylene glycol groups, PEG-DMA, dimethacrylate with one or more lactic acid groups, dimethacrylate with one or more HEMA groups, a molecule that can be co-polymerized with vinyl acetate, and has two or more end groups comprised of acrylate groups.

According to one aspect of the invention, the hydrolysis can be carried out in a basic alcohol solution, such as methanol and KOH, the methanol is added first and allowed to swell the polymer network completely or partially before addition of the KOH.

According to another aspect, the hydrolysis can be carried out in a solution containing a blend of solvents having at least one solvent that has an affinity for the first crosslinked polymer network and at least one solvent with an affinity for the hydrolyzed polymer network, wherein the first solvent is methanol and the second solvent is DMSO.

According to another aspect of the invention, additional one or more molecules can be added to the hydrogel composition, for example, a molecule that has a mono-functional methacrylate group, one or more ethylene glycol groups, polyethylene glycol methyl ether methacrylate (PEG-MeMA), mono-methacrylate with one or more lactic acid groups, monoacrylate terminator, mono-methacrylate with one or more saccharide groups, wherein the saccharide group can be chondroitin sulfate.

According to another aspect, hydrogel composition comprises additional ingredient(s) that does not polymerize.

In one aspect of the invention, a mold can be used to control the shape of the polymer network, wherein the material of the mold governs the surface finish of the polymer network.

According to another aspect, the crosslinked network surface can be exposed to further mono-functional molecules and polymerized to modify the surface relative to the bulk, wherein the mono-functional molecule can be PEG-MeMA, for example.

According to another aspect, the monomer can be polymerized into a porous material, wherein the porous material can be a porous metal substrate.

According to another aspect, the monomer can be co-polymerized with another monomer unit that covalently binds to the vinyl acetate chains or the monomer can be co-polymerized with acrylic acid monomers According to another aspect, the hydrophilic polymer network can be subsequently implanted into a human body or the hydrophilic polymer network can be implanted in cartilage in a human joint, such as into a hole present in the cartilage.

According to another aspect, the hydrophilic polymer network can be manufactured as a thread or filament.

According to another aspect of the invention, the porosity of the hydrogel governs the rate of release of a drug.

In another aspect, the invention provides hydrogels made by any of the methods disclosed herein. For example, in one aspect, the invention provides hydrolyzed cross-linked hydrogels made by a method comprising the steps of: a) polymerizing a monomer in the presence of a crosslinking agent, thereby producing a crosslinked polymer network; and b) hydrolyzing the crosslinked polymer network, thereby forming a hydrogel having hydrophilic polymer network.

In another aspect, the invention provides hydrolyzed cross-linked poly(vinyl alcohol) (PVA)-hydrogels made by a method comprising the steps of: a) polymerizing vinyl acetate (VAc) monomers by chemical-crosslinking, thereby producing a poly(vinyl acetate) (PVAc) polymer network; and b) hydrolyzing the crosslinked PVAc polymer network, thereby forming a hydrolyzed PVA-hydrogel.

In another embodiment, the invention provides methods of polymerizing a monomer in the presence of a crosslinker to form a network, and then hydrolyzing the network. The methods can be generally related to the methods for making PVA microspheres. The methods also can include step of the addition of mono-functional groups during the polymerization process to provide end-tethered molecules that are not involved structurally, but are responsible for unusual mechanical properties or modified lubricity. In an aspect, the invention provides methods including steps of polymerization of a hydrolysable monomer (VAc for example) with a chemical crosslinker (at least one difunctional molecule such as PEG-DMA, diallyl succinate, polyethylene glycol divinyl ether, or butanediol diacrylate) along with single ended chains to mimic GAGs (glycosaminoglycans) in cartilage. These chains could be PEG-MeMA or others. These steps resulting in a tough and lubricious, highly hydrated hydrogel with a primarily PVA backbone, hydrophilic crosslinkers of varying lengths and "pendant" chains which influence the surface chemistry and lubricity of the gel, as well as the hydrophilicity of the gel.

In another aspect, the invention provides methods for making a hydrolyzed cross-linked hydrogel comprising the steps of: (a) polymerizing a monomer in the presence of a crosslinking agent and one or more molecules, thereby producing a crosslinked polymer network containing pendant chains; (b) hydrolyzing the crosslinked polymer network, thereby forming a hydrogel having hydrophilic polymer network; and (c) hydrating the polymer network, thereby forming a hydrolyzed cross-linked hydrogel having a hydrophilic network and pendant chains.

In yet another aspect, the invention provides methods of making a hydrolyzed cross-linked poly(vinyl alcohol) (PVA)-hydrogel, wherein the method comprises the steps of: (a) polymerizing vinyl acetate (VAc) monomers in the presence of a crosslinking agent and one or more molecules, thereby producing a crosslinked poly(vinyl acetate) (PVAc) polymer network containing pendant chains; (b) hydrolyzing the crosslinked PVAc polymer network, thereby forming a hydrogel having hydrophilic PVAc polymer network; and (c) hydrating the PVAc polymer network, thereby forming a hydrolyzed cross-linked hydrogel having a hydrophilic PVAc polymer network and pendant chains.

In still another aspect, the invention provides hydrolyzed cross-linked hydrogels made by a method comprising the steps of: (a) polymerizing a monomer in the presence of a crosslinking agent and one or more molecules, thereby producing a crosslinked polymer network containing pendant chains; (b) hydrolyzing the crosslinked polymer network, thereby forming a hydrogel having hydrophilic polymer network; and (c) hydrating the polymer network, thereby forming a hydrolyzed cross-linked hydrogel having a hydrophilic network and pendant chains.

Yet, in another aspect, the invention provides hydrolyzed cross-linked poly(vinyl alcohol) (PVA)-hydrogels made by a method comprising the steps of: (a) polymerizing vinyl acetate (VAc) monomers in the presence of a crosslinking agent and one or more molecules, thereby producing a crosslinked poly(vinyl acetate) (PVAc) polymer network containing pendant chains; (b) hydrolyzing the crosslinked PVAc polymer network, thereby forming a hydrogel having hydrophilic PVAc polymer network; and (c) hydrating the PVAc polymer network, thereby forming a hydrolyzed cross-linked hydrogel having a hydrophilic PVAc polymer network and pendant chains.

Unless otherwise defined, all technical and scientific terms used herein in their various grammatical forms have the same meaning as commonly understood by one of ordinary skill in the art to which this invention belongs. Although methods and materials similar to those described herein can be used in the practice or testing of the present invention, the preferred methods and materials are described below. In case of conflict, the present specification, including definitions, will control. In addition, the materials, methods, and examples are illustrative only and are not limiting.

Further features, objects, advantages, and aspects of the present invention are apparent in the claims and the detailed description that follows. It should be understood, however, that the detailed description and the specific examples, while indicating preferred aspects of the invention, are given by way of illustration only, since various changes and modifications within the spirit and scope of the invention will become apparent to those skilled in the art from this detailed description.

DETAILED DESCRIPTION OF THE INVENTION

Figure 1:
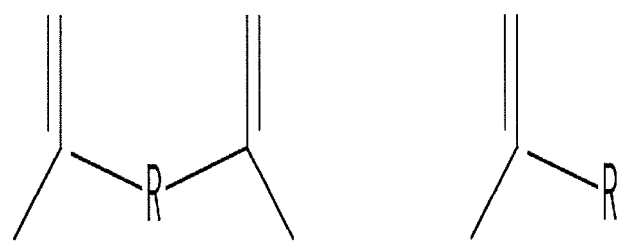
FIG. 1 depicts generic molecular structures of cross-linker (Left), pendant groups (Right). 'R' represents any suitable chemical structure including monomers and polymers.

The present invention provides methods of making hydrolyzed cross-linked poly(vinyl alcohol) (PVA) hydrogels by polymerizing vinyl acetate (VAc) monomers to poly(vinyl acetate) (PVAc) polymer network by chemical-crosslinking and hydrolysis. The invention also provides the materials produced and use of the cross-linked hydrolyzed PVA hydrogels. The invention also provides methods for incorporating pendant chains in the hydrogel during the polymerization process. The invention further provides hydrogels containing mono-functional copolymerized moieties which provide lubrication. Other advantages and advances provided by the invention are discussed herein.

The usual methods of manufacturing PVA hydrogels is through crosslinking of PVA polymers directly. This crosslinking can occur through chemical means, irradiation, or through a physical mechanism such as freeze-thaw or the "Thetagel" process (see U.S. Pat. Nos. 7,619,009 and 7,485,670), which does not employ the preceding approaches. Once crosslinked, the PVA chains hydrate in water and swell the structure to form a swollen hydrogel. PVA is manufactured from the hydrolysis of poly(vinyl acetate) through the exchange of the (C=O)—CH3 groups with a hydrogen rendering the polymer water soluble.

By polymerizing vinyl acetate along with a di-methacrylate-functional monomer/polymer, crosslinks can be polymerized directly into the PVAc polymer, creating a continuous VAc network. Polymerizing a mono-methacrylate monomer/polymer creates pendant chains covalently attached to the PVAc. Subsequent hydrolysis converts the crosslinked PVAc network to a crosslinked PVA network resulting in chemically crosslinked PVA hydrogel with, if desired, pendant chains.

Pendant chains as described, refer to a monomer or polymer that is joined to the surrounding network in such a way that the chain is attached at one end and free to move at the other end. For example, a poly(ethylene glycol) monomethacrylate (PEG-MeMA) would be attached to the network at the monomethacrylate end of the chain, but the other end of the chain would not be fixed but would instead be free to move in the solvent. A group of these "pendant chains" on a solids substrate would be considered a "polymer brush" in the literature. This phrase is used in the art. Alternative phrases to described a "pendant chain" would be an "end-grafted polymer" or "dangling chain."

Network or polymer network, in this context refers to a continuous polymer chain that splits and rejoins to form a space-filling, single molecule. Multiple networks could be interdigitated as occurs in "interpenetrating networks" also known as IPNs, which are well known in the art. The terms "network" and "pendant chain" are further defined in: Jenkins, A. D., et al., *GLOSSARY OF BASIC TERMS IN POLYMER SCIENCE* (*IUPAC Recommendations* 1996). Pure and Applied Chemistry, 1996. 68(8): p. 1591-1595.

The present invention can employ PVA-based materials that are prepared by forming a chemically-crosslinked PVAc article, swelling in alcohol, and subsequently hydrolyzing to form a chemically crosslinked PVA article. In addition, the invention can contain mono-functional copolymerized moieties which can provide lubrication, or other functionality.

PVA can be made by hydrolysis of a suitable polymer, usually PVAc. PVAc is usually manufactured through a bulk polymerization process where the chain is grown linearly. The process of the polymerization involves breaking of the C=C bond on the vinyl acetate group. Thus, replacing the vinyl acetate groups with some other molecule with a similar structure will allow the polymerization to proceed as before, but with different groups from the VAc groups. If these groups are bi-functional, they will crosslink. If they are mono-functional, they will end up being pendant chains. In one aspect, the preferred crosslinkers can be those composed of ethylene glycol groups terminated with methacrylate groups (such as ethyleneglycol dimethacrylate (EG-DMA) or polyethyleneglycol dimethacrylate (PEG-DMA)). However, other crosslinkers are possible, such as 1,4-butanediol dimethacrylate, urethane dimethacrylate dimethyl siloxane dimethacrylate, vinyl methacrylate and any other similar molecules known in the art. An example of a suitable generic structure is shown in FIG. 1. Likewise, the mono-functional molecule can be any suitable chemistry, such as glycerol monomethacrylate, methylpropane-1,3-diol-monomethacrylate and propylene Glycol Monomethacrylate, 2-hydroxypropyl methacrylate, dimethyl siloxane methacrylate, etc. Implicitly, each of these groups in the crosslinker or the pendant chain may be a monomer or multiple-monomers, or a polymer. In the case where there is more than one group in the chain, these groups need not be the same chemistry (resulting in a co-polymer). Other chemistries known are allyl methacrylate, ethylene glycol dimethacrylate, HALEMA-2 (2-allyloxyethyl methacrylate), DMA/Q4-3667 (polyethyleneoxide dimethylsiloxane block copolymer: dimethacrylate), vinyl methacrylate, etc. See for example, European Patent No. EP 0108886.

According to an embodiment of the invention, by adding a non-crosslinking ingredient, a pore structure can be imprinted on the gel, thereby creating a hydrogel with controlled porosity. The crosslinking groups and pendant groups need not have the same chemistry, or molecular weight. For example, the crosslinkers could be short-chain ethyleneglycol dimethacrylate (EG-DMA), whereas the pendant chains could be longer poly(ethyleneglycol) monomethacrylate (PEG-MeMA), or the crosslinker could be a longer chain. The chemistry could be chosen to include charges, etc. Any molecule that possesses suitable "active" end-groups can be used, including degradeable molecules such as polylactic acid. A long chain crosslink may impart resilience to the hydrogel by not aggressively pinning the crosslinks together, thus allowing greater deformation before failure.

Figure 2:
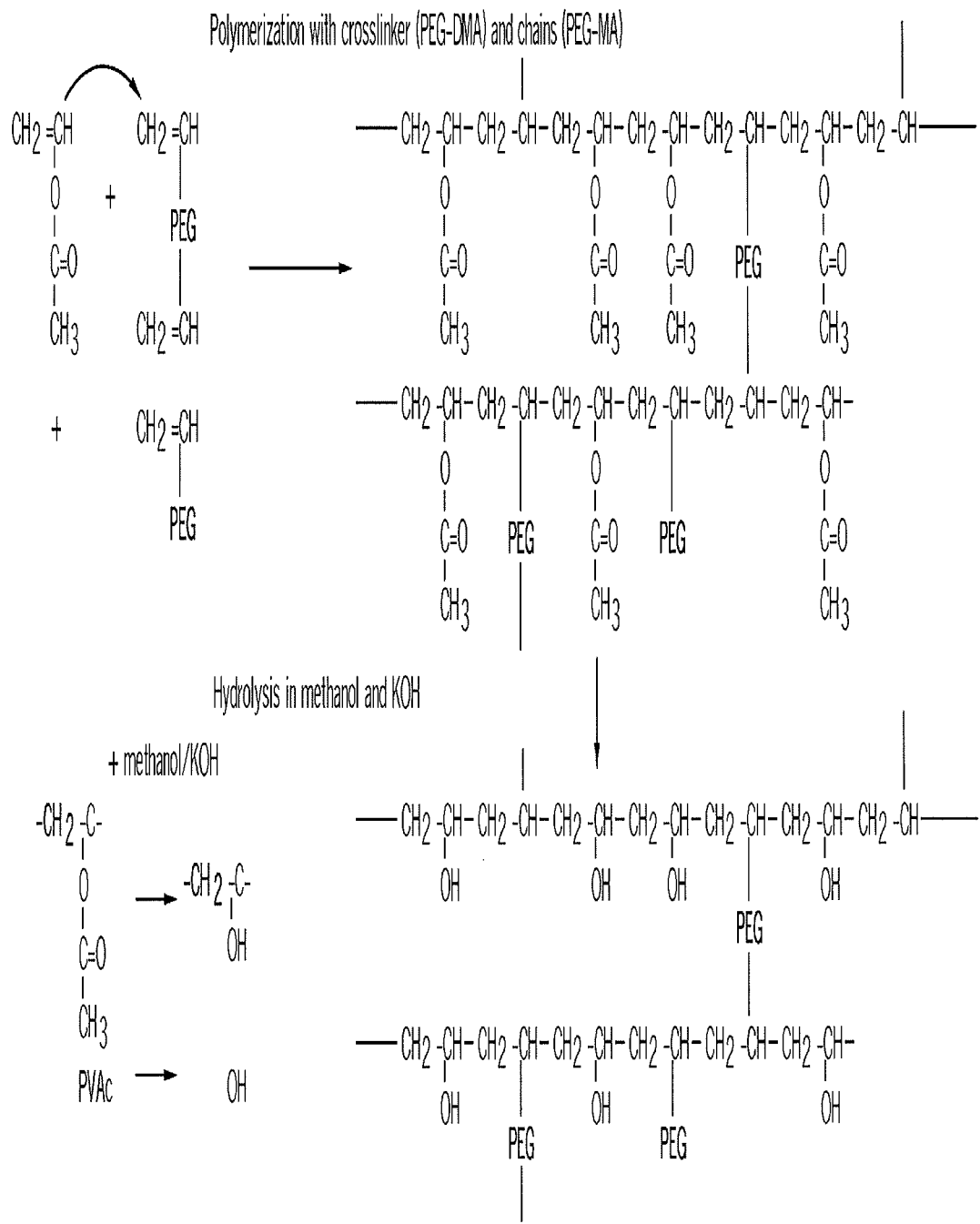
FIG. 2 illustrates a schematic method of making PVA-hydrogel and the chemical structures.
Figure 3:
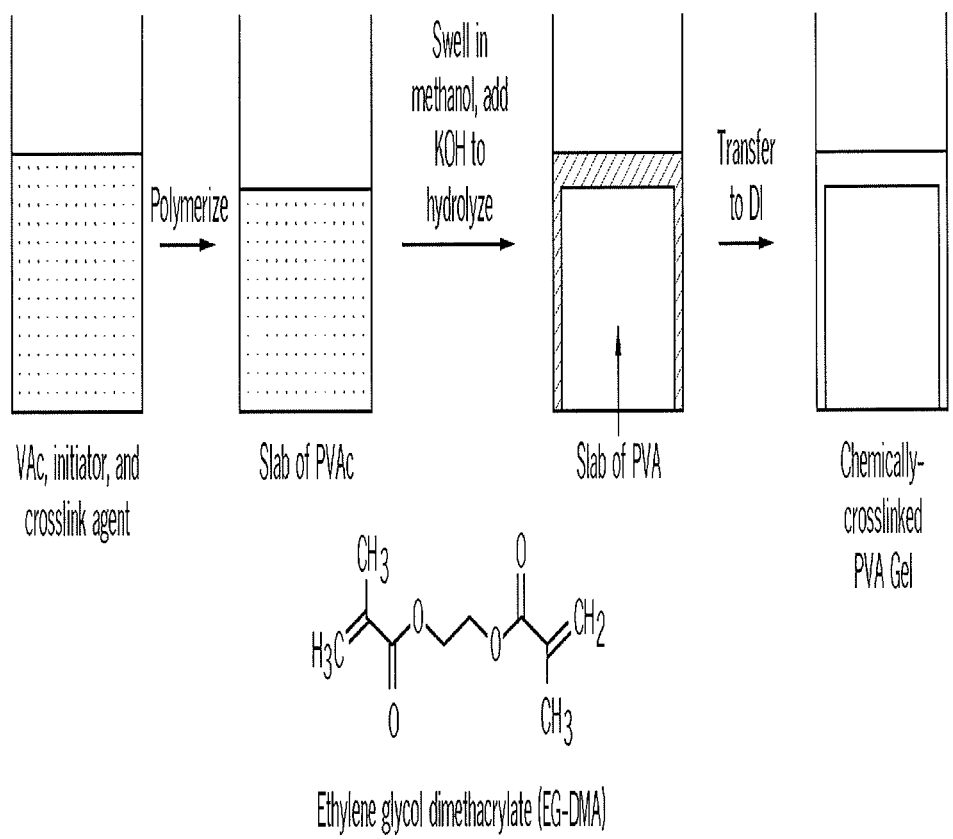
FIG. 3 illustrates schematic of a manufacture procedure.

The hydrolysis step requires diffusion of methanol or some other suitable solvent into the PVAc. This feature can be used to control the level of hydrolysis in the component, creating a gradient from the outside in. Schematic methods of making PVA-hydrogel and the chemical structures are shown in FIG. 2. FIG. 3 illustrates a step by step method of manufacturing hydrolyzed cross-linked hydrogel. The method provides in-situ polymerized crosslinked PVA hydrogel with improves strength while maintaining high lubricity.

One aspect of the invention provides a method step of adding an inert filler, such as non-functional poly(ethylene glycol) or glycerol or end-capped vinyl acetate. This inert filler can fully dissolve with the VAc, thus simply providing volume for the reaction to proceed, or it can be partially or completely incompatible with the VAc resulting in phase separation of the inert filler and the VAc. The final crosslinked network would therefore have a porous structure, where once hydrolyzed the "bridges" of the network are composed of PVA hydrogel, and the pores are substantially free of PVA.

During the hydrolysis step, conventionally the PVAc network is swollen in methanol, but once the PVAc is converted to PVA it is no longer soluble in methanol. Thus, a substantially hydrolyzed PVA network precipitates in methanol and the network collapses. To avoid this, a solvent can be used that is compatible with both VAc and VA, ensuring that the network stays partially or completely swollen as it is hydrolyzed, allowing greater control of the final structure, including the possibility of gradients in crosslink density. This solvent can be a single solvent, or a blend of solvents, such as methanol and DMSO. By allowing partially swelling of the PVAc before the addition of KOH, the hydrolyzation levels can be varied from the surface to the bulk.

The surface finish of the completed gels has been observed to be different depending on the contact mold surface. For example, PTFE produces a different surface, as measured by Coefficient of Friction, than a free surface. Likewise stainless steel also produces a different surface.

It can be advantageous to have the crosslinker non-water soluble, while the pendant chains are water soluble. This arrangement can ensure that the crosslinker had similar solubility to the VAc monomer, thus potentially allowing more even swelling. Once hydrolyzed, this group would not be solvated by water, but this may provide a toughening function to the hydrogel. In addition, the crosslinker can be vinyl acetate which would hydrolyze in an identical fashion to the main-chain of the network.

In addition, during the polymerization step, and before hydrolysis, it is possible to immerse the partially completed network in a solution of PEG-MeMA chains to build a surface layer to enhance the surface and lower its COF even further. The system can also be polymerized into a suitable porous material, such as trabecular metal to aid in fixation in an in vivo application. The material is suitable for cartilage repair (osteochondral plugs), cartilage resurfacing, interpositional devices or complete bearing surfaces. The material can also be copolymerized with acrylic acid for an even more hydrophilic system, potentially with faster swelling kinetics. The resulting hydrogel can be seeded with fibroblasts for mechanically activated cell differentiation (can lead to matrix in growth) or used in drug-release. This construct also has application as an anti-thrombogenic wound closure device, possibly with slow localized release of clotting factors, due to its high hydrophilicity.

The poly(ethyleneglycol) dimethacrylate (PEG-DMA), as described herein, can encompass any molecule with an ethylene glycol chain and methacrylate end-groups such as ethylene glycol dimethacrylate (EG-DMA), triethylene glycol dimethacrylate and poly(ethylene glycol) dimethacrylate.

The poly(ethyleneglycol) monomethacrylate (PEG-MeMA), as described herein, can encompass any molecule with an ethylene glycol chain and one methacrylate end-group such as ethylene glycol monomethacrylate (EG-MeMA), triethylene glycol monomethacrylate and poly(ethylene glycol) monomethacrylate (PEG-MeMA).

Manipulation of Structure

Figure 8:
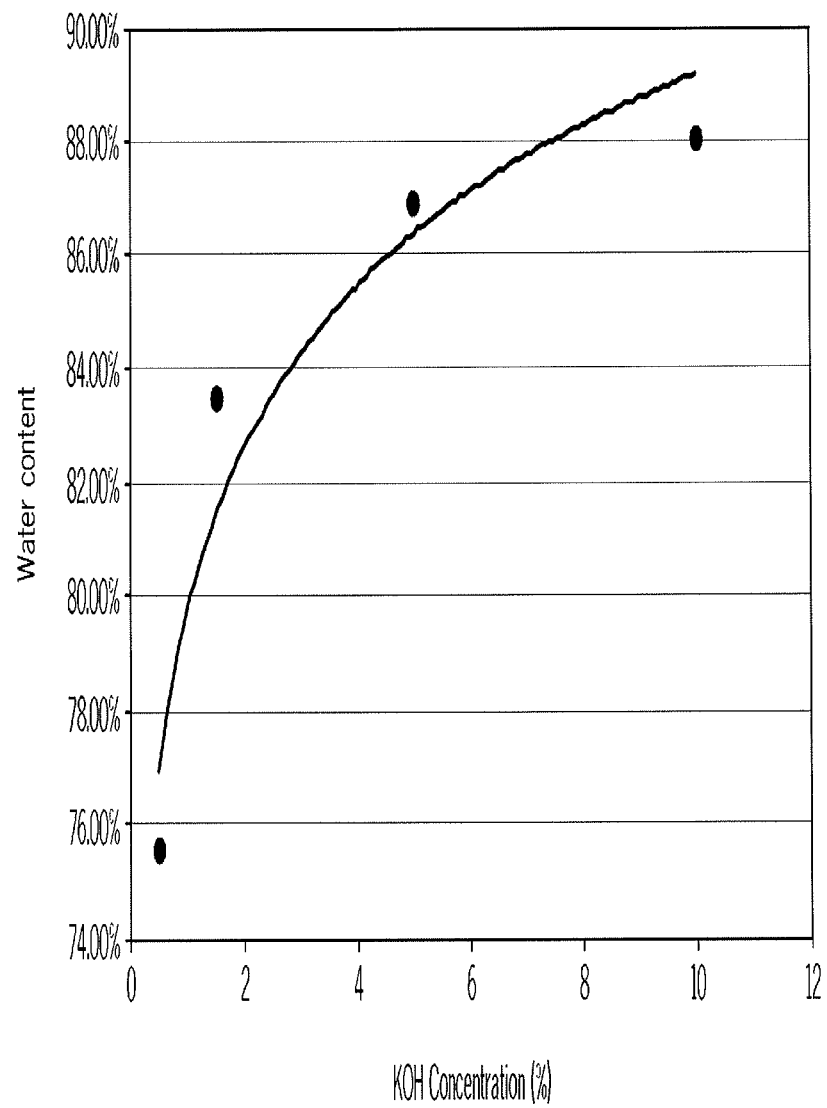
FIG. 8 shows final water content versus hydrolyzing solution concentration.
Figure 9:
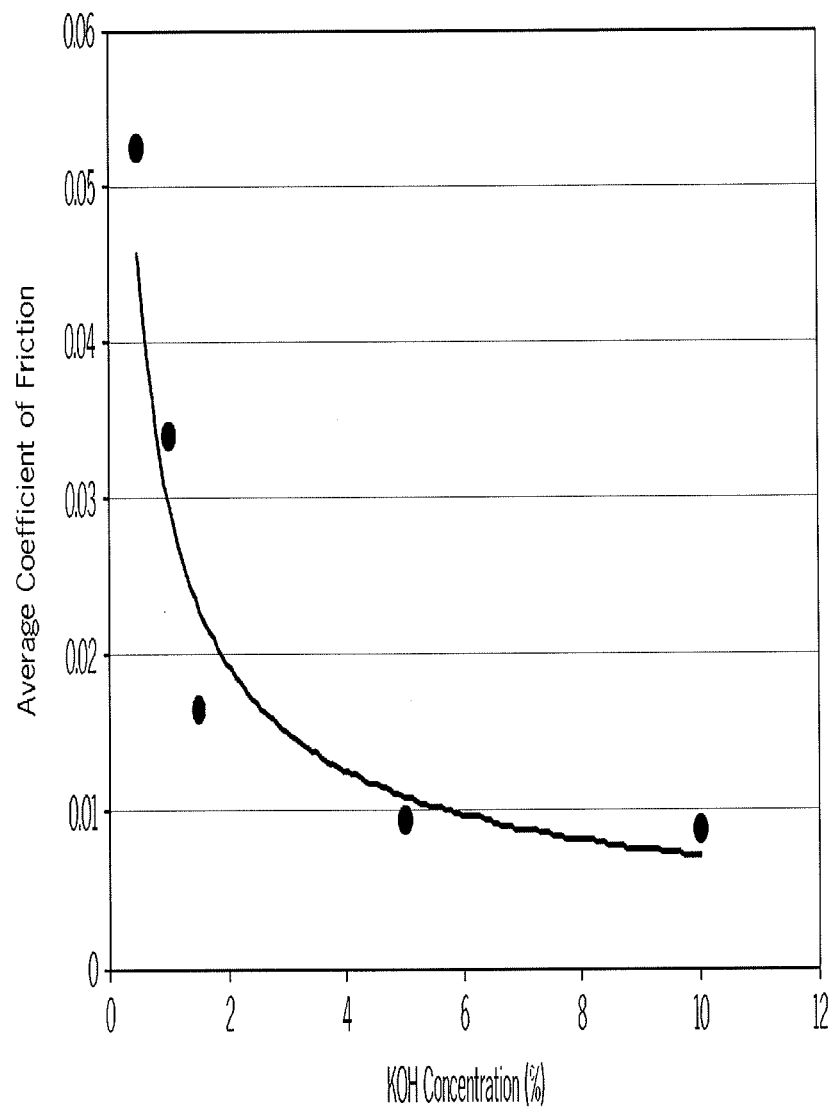
FIG. 9 shows average coefficient of friction versus hydrolyzing solution concentration.
Figure 10:
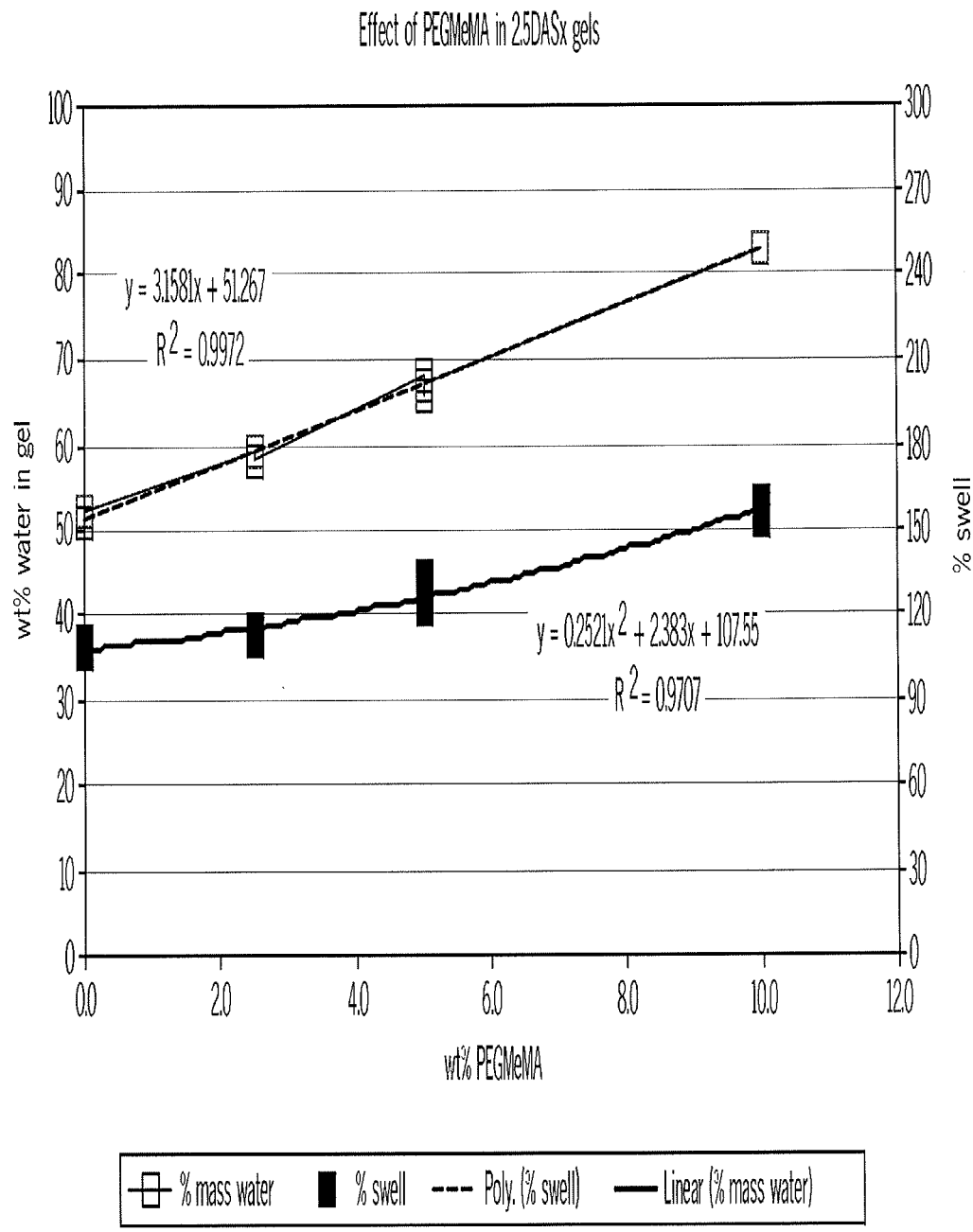
FIG. 10 illustrates the influence of PEG-MeMA on the water content of the resulting hydrogels.

The rate of reaction of the individual monomers, crosslinkers and pendant chains can be used to manipulate the final structure of the hydrogel. For example, if the VAc reacts faster than the crosslinking groups the VAc chains will grow significantly faster than they crosslink. A higher molecular weight between crosslinks will result (lower crosslink density) and in some cases it would be possible to form two distinct networks, so-called IPNs (interpenetrating networks) of long chain PVAc entangled with a crosslinked VAc/PEG network. Mixed solvents can be used to manipulate diffusion rate during the hydrolysis steps, allowing the generation of partially hydrolyzed stiffer hydrogels that retain a different surface from the core. Control of the time of hydrolysis also has an impact on the mechanical properties of the hydrogels. Partially hydrolyzing the entire hydrogel component will also influence the mechanical properties (Table 1), water content (FIG. 8), and the coefficient of friction (FIG. 9).

TABLE 1

Hydrolysis time versus creep for 5PEG2.5 formulation. Shorter hydrolysis time leads to less deformation and more complete recovery.

| Hydrolysis time [hr] | Initial creep strain | Final creep strain | Recovery Strain |
|---|---|---|---|
| 4 | 30% | 42% | 10% |
| 8 | 35% | 50% | 12% |
| 24 | 40% | 62% | 20% |
| 48 | 52% | 72% | 35% |

Degradation

Choices of specific crosslinking chemistries allow manipulation of the final hydrogel including is degradability. For example, the crosslinkers described herein can be degradable molecules that will be attacked by specific processes in the body, thus rendering the entire hydrogel biodegradable. Since the components of the hydrogel are PVA and PEG groups primarily, the materials released by this degradation are relatively benign. For example, a high ester content in the crosslinkers would lead to degradation via enzymatic cleavage. The polymer network can be fully or partially degradable via enzymatic cleavage of specific chemistries in the crosslinking molecule (one example of possible enzymes is the ubiquitous esterase enzyme; carboxylase may also work). Parameters that may be used to govern the degradation of the network are the crosslink density of the polymer system, the percent vinyl alcohol content and the chain average molecular weight (Mc) of PVA. The number of hydrolysable groups in the crosslinker molecule governs the rate of degradation of the polymer network (Butanediol diacrylate and 1,6-Hexanediylbis[oxy(2-hydroxy-3,1-propanediyl)]bisacrylate would be suitable degradeable crosslinkers).

Molecule Activity

In addition, the pendant group could be chosen to reflect a different molecule, i.e. instead of a methacrylate termined PEG molecule, the molecule could be any functional chemistry with a suitable moiety (in this case methacrylate) to allow it to polymerize in to the structure of the organogel. The chemistry could be chosen from any hydrophilic or hydrophobic molecule, including (but not limited to) molecules analogous to the glycosaminoglycans in the body. An example of such a molecule would be polyelectrolyte chains such as PNaSS (poly(sodium 4-styrenesulfonate) or a polysaccharide such as chondroitin sulfate or its repeat units or family members (Dermatan sulfate Keratan sulfate Heparin Heparan sulfate Hyaluronan).

DEFINITIONS

The terms "about" and "approximately" in the context of numerical values and ranges refers to values or ranges that approximate or are close to the recited values or ranges such that the invention can perform as intended, such as having a desired degree of cross-linking, creep resistance, lubricity, etc., as is apparent to the skilled person from the teachings contained herein. This is due, at least in part, to the varying properties of polymer compositions. Thus, these terms encompass values beyond those resulting from systematic error. These terms make explicit what is implicit.

Numerical ranges are understood to be an efficient and concise approach for setting forth all values within the range. Thus, a range expressly discloses all integers and fractional values within the range, and all sub ranges as well. By way of example, a range of 1 to 10 (1-10) would expressly set forth 1, 1.1, 1.22, 1.305, ... 9.7, 9.81, 9.9, 9.95, 9.998, 10, along with all sub ranges, e.g., 2.32 to 5.561; 7.3 to 9.75, etc. Ranges also can be described with "about" and "approximately".

The term "hydrogel" or the term "PVA-hydrogels", as described herein, encompasses polymer-based hydrogels, including PVA-based hydrogels, and all other hydrogel compositions disclosed herein including hydrolyzed hydrogels. PVA-hydrogels are continuous networks of hydrophilic polymers containing absorbed water that can absorb a large amounts of energy, such as mechanical energy, before failure.

"Thetagels" are disclosed and defined in U.S. Pat. Nos. 7,619,009 and 7,485,670, and U.S. publication number 2004/0092653A1. Thetagels can be formed by changing solvent conditions from those that do not favor gelation to those that favor gelation. Often the terms "good", "bad" or "poor" are used to describe solvents and solvent conditions.

"Creep resistance" (creep resistant) generally refers to the resistance to continued extension or deformation, which results from the viscoelastic flow of the polymer chains under continuous load.

"Lubricity" (lubricious) generally refers to a physical property of a hydrogel, for example, it is a measure of the slipperiness of a hydrogel surface, which also relates to the hydrophilicity of the same surface.

"Coefficient of friction" (COF) generally refers to the coefficient of friction between two solid surfaces, which is defined as the ratio of the tangential force required to produce sliding divided by the normal force between the surfaces.

Each composition and attendant aspects, and each method and attendant aspects, which are described above can be combined with another in a manner consistent with the teachings contained herein. According to the embodiments of the inventions, all methods and the steps in each method can be applied in any order and repeated as many times in a manner consistent with the teachings contained herein.

The invention is further described by the following examples, which do not limit the invention in any manner.

EXAMPLES

Example 1

Figure 4:
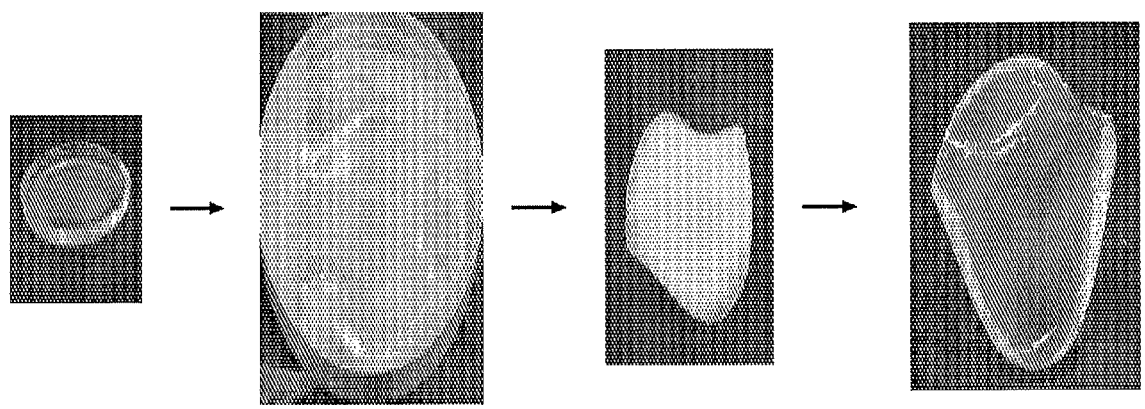
FIG. 4 depicts images of PVA hydrogel at different steps of production: (i) Crosslinked poly(vinyl acetate) (PVAc) puck after polymerization (diameter=6 cm); (ii) PVAc swollen in methanol for 4 hours at 40° C.; (iii) Shrunken poly(vinyl alcohol) (PVA) puck after hydrolysis with potassium hydroxide in methanol; and (iv) PVA hydrogel after equilibration in DI water for 3 days.

Preliminary studies were focused on preparing in-situ polymerized vinyl acetate pucks with small amounts of PEG-DMA (about 2-5 wt %) as a crosslinking agent. These pucks were then swollen in methanol and hydrolyzed with potassium hydroxide (KOH) to convert the poly(vinyl acetate) to PVA. It was noticed that the gels prepared by this technique were highly elastic, relatively strong, and highly lubricious. The equilibrium water content of the hydrogels post-processing was found to scale inversely with crosslinker content, as would be expected with a crosslinked gel. It was also found that incorporating a small amount of mono-functional PEG (PEG-MeMA, $M_n$=about 475) improved the smoothness of the surfaces of the hydrogels and made them more lubricious. As increasing amounts of PEG-MeMA were added, the samples became more lubricious and also less stiff. In these preliminary studies, it was observed that using 5 wt % PEG-DMA crosslinker and 2.5 wt % PEG-MeMA provided a good combination of reproducibility, stiffness, and lubriciousness (see FIG. 4). FIG. 4 shows images of PVA hydrogel at different steps of production: (i) Crosslinked poly(vinyl acetate) (PVAc) puck after polymerization (diameter=6 cm); (ii) PVAc swollen in methanol for 4 hours at 40° C.; (iii) Shrunken poly(vinyl alcohol) (PVA) puck after hydrolysis with potassium hydroxide in methanol; and (iv) PVA hydrogel after equilibration in DI water for 3 days.

Example 2

Preliminary tests were performed on a PVA-co-PEG 5-2.5 hydrogel (that is, 5 wt % PEG-DMA and 2.5 wt % PEG-MeMA) formulation to determine its feasibility for use in the CMC joint. This formulation was chosen after preliminary studies indicated that it was easy to produce and had mechanical properties that appeared qualitatively suitable. Similar tests were also performed on two physically-crosslinked PVA-based hydrogels to compare the materials produced by the methods disclosed herein to other PVA-based technologies. One such gel was prepared by freeze-thaw cycling a 20% PVA ($M_w$ about 250,000) solution five times (20% PVA 5 FT). The other was prepared by dissolving 25% PVA ($M_w$ about 250,000) and 28% polyethylene glycol ($M_n$=400) in water at 90° C. and allowing the solution to gel at room temperature (that is, 25%-28% Thetagel). This material is termed a 'Thetagel' because it gels due to a transition from a good solvent condition to a poor solvent condition and can be understood according to the 'Theta' temperature of Flory (see Flory, P. J., *Principles of Polymer Chemistry*. Cornell University Press: Ithaca and London, 1953). The 20% PVA 5 FT (that is, 20% PVA solution freeze-thawed five times) and the 25%-28% Thetagel (that is, 25% PVA solution and 28% PEG 400 as gellant) formulations were chosen because they had similar equilibrium water contents (EWC) to the PVA-co-PEG 5-2.5 (5 wt % PEG-DMA and 2.5 wt % PEG-MeMA) formulation (EWC about 80%) after equilibration in deionized water. The goals of the preliminary characterization were two-fold: first, to determine whether the chemically-crosslinked PVA-co-PEG system is an improvement over existing PVA hydrogel technologies, and second, to determine whether the PVA-co-PEG materials produced by the methods disclosed herein show the potential for survival in the CMC joint.

TABLE 2

List of the three hydrogel formulations subjected to preliminary mechanical tests.

| Hydrogel Name | Crosslink Type | Composition | EWC, % |
| --- | --- | --- | --- |
| PVA-co-PEG 5-2.5 | Chemical | PVA + (5% PEG-DMA and 2.5% PEG-MeMA) | 80% |
| 20% PVA 5 FT | Physical | 20% PVA solution freeze-thawed five times | 78% |
| 25%-28% Thetagel | Physical | 25% PVA solution, 28% PEG 400 as gellant | 80% |

Creep Resistance

Figure 5:
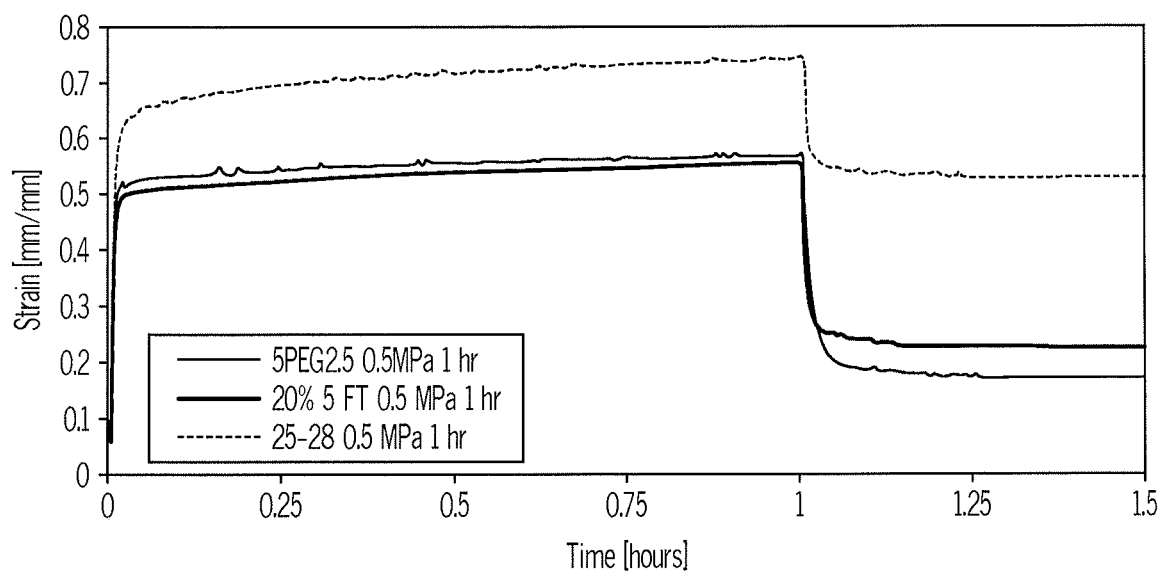
FIG. 5 shows representative creep curves for PVA-co-PEG 5-2.5 (5 wt % PEG-DMA and 2.5 wt % PEG-MeMA) hydrogel (bottom curve) and also a freeze-thawed (20% PVA 5 FT) PVA hydrogel and a PVA Thetagel (top curve). The figure also depicts a representative sample before and after testing to show the effect of loading on the sample dimensions.
Figure 5:
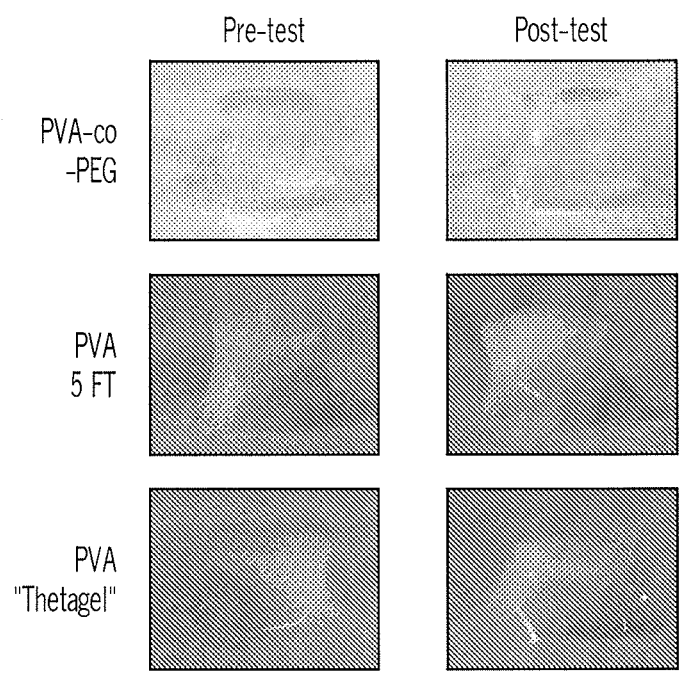

FIG. 5 shows representative creep curves for the three formulations tested in the study. The creep strain of the PVA-co-PEG 5-2.5 (5 wt % PEG-DMA and 2.5 wt % PEG-MeMA) gel at 0.5 MPa after one hour is less than that of the 25%-28% Thetagel (25% PVA solution and 28% PEG 400 as gellant) but slightly higher than that of the 20% PVA 5 FT gel (20% PVA solution freeze-thawed five times). The strain upon unloading to 0.05 MPa shows the Thetagel as recovering the least, although the 5PEG2.5 (5 wt % PEG-DMA and 2.5 wt % PEG-MeMA) gel clearly recovers more than the other two hydrogels. Since the unloading step still had a finite load, it does not give a clear indication of which formulation actually has the most complete strain recovery after complete unloading to zero load. In addition, the viscoelastic nature of these materials means that they take time to recover, much like natural cartilage. The non-porous indenter also acts to slow this hydration by limiting access of the solvent to the hydrogel on relaxation. To augment the creep data, pictures of samples before and after testing are also included in FIG. 5. It can be seen that the PVA-co-PEG system has returns to essentially the same shape (measurements with a set of calipers revealed no significant difference in height after testing). The 20% PVA 5 FT (that is, 20% PVA solution freeze-thawed five times) formulation had a slightly flattened shape after testing, with a loss in height on average of about 5%. The 25%-28% Thetagel (25% PVA solution and 28% PEG 400 as gellant) suffered the greatest permanent deformation of all three formulations, as is clearly evident from the images in FIG. 5. Overall, the creep response of the PVA-co-PEG 5-2.5 (that is, 5 wt % PEG-DMA and 2.5 wt % PEG-MeMA) formulation is closer in nature to the 20% PVA 5 FT gel than it is to the 25%-28% Thetagel (25% PVA solution and 28% PEG 400 as gellant), while the PVA-co-PEG gel recovers more of its initial height than the other gels. FIG. 5 shows representative creep curves for PVA-co-PEG 5-2.5 (5 wt % PEG-DMA and 2.5 wt % PEG-MeMA) hydrogel (bottom curve) and also a freeze-thawed (20% PVA solution freeze-thawed five times) PVA hydrogel and a PVA Thetagel (top curve). The figure also depicts a representative sample before and after testing to show the effect of loading on the sample dimensions.

Modulus

Figure 6:
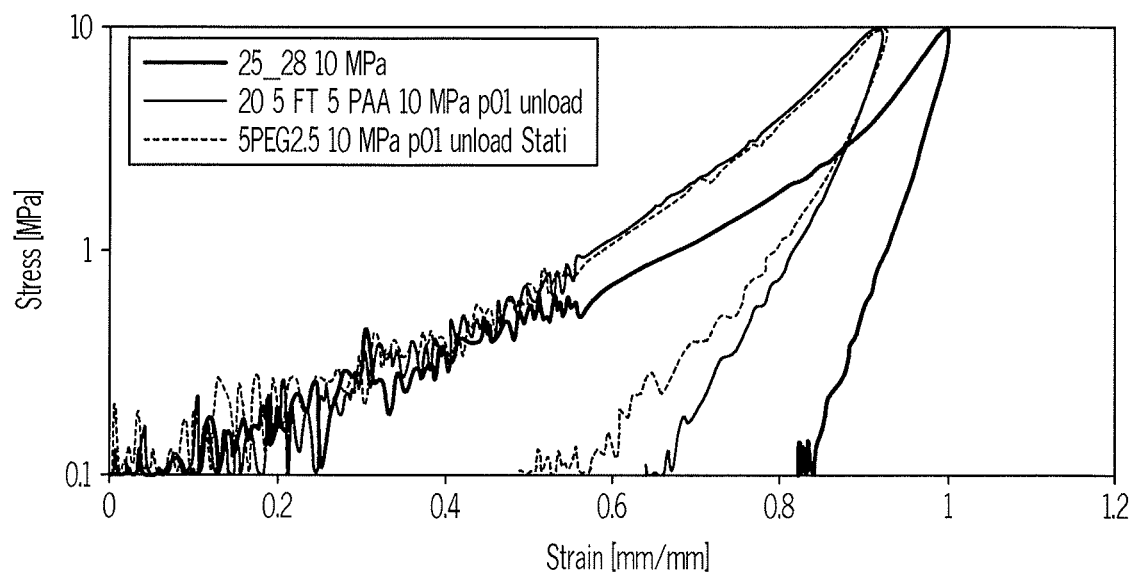
FIG. 6 shows representative stress-strain curves for PVA-co-PEG 5-2.5 (5 wt % PEG-DMA and 2.5 wt % PEG-MeMA) hydrogel, a freeze-thawed (20% PVA 5 FT) PVA hydrogel and PVA Thetagel. Tests run in DI water at 40° C. Inset shows images of samples before (Left) and after (Right) testing.
Figure 6:
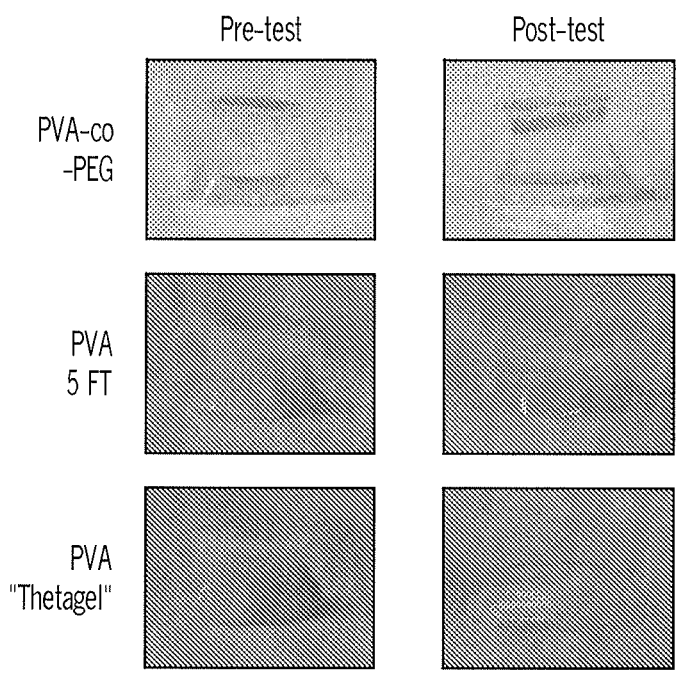

A peak load of 10 MPa was chosen for the stress-strain tests, corresponding to a load of approximately 150 kg in a 1.6 cm$^2$ (0.25 in$^2$) contact area. The loading cycle involved loading to 10 MPa at a rate of 0.3 MPa/min followed by immediate unloading at a rate of 0.3 MPa/min. The rate was slower than "instantaneous" due to limitations in the testing apparatus. Tests were run in deionized water at 40° C. Stress-strain data for the three gels are shown in FIG. 6. FIG. 6 shows representative stress-strain curves for PVA-co-PEG 5-2.5 (5 wt % PEG-DMA and 2.5 wt % PEG-MeMA) hydrogel, a freeze-thawed (20% PVA solution freeze-thawed five times) PVA hydrogel and PVA Thetagel. All gels show initially a relatively flat stress-strain profile, indicating a high degree of deformability at low loads. However, above a strain of approximately 60% compression, all three gels show significant strain-hardening. The final strain at the end of the loading cycle was very high for all samples, although the PVA-co-PEG and the 5 FT samples had significantly lower maximum strains (85-90%) than did the Thetagel samples (95%). The strain recovery was also much more pronounced in the PVA-co-PEG 5-2.5 (5 wt % PEG-DMA and 2.5 wt % PEG-MeMA) and the PVA 5 FT (20% PVA solution freeze-thawed five times) gels, with each recovering a significant percentage of its original height after unloading. The recovery of the PVA-co-PEG sample, as seen in the inset in FIG. 6, is nearly complete, with the only change in shape a slight widening at the top of the sample. The PVA 5 FT (that is, 20% PVA solution freeze-thawed five times) sample shows a more significant increase in diameter and concomitant reduction in height. FIG. 6 inset shows images of samples before (Left) and after (Right) testing. The 25%-28% Thetagel (25% PVA solution and 28% PEG 400 as gellant) was crushed from a cylindrical shape into a pancake type shape, from which it did not recover, although it did not tear.

Coefficient of Friction

Figure 7:
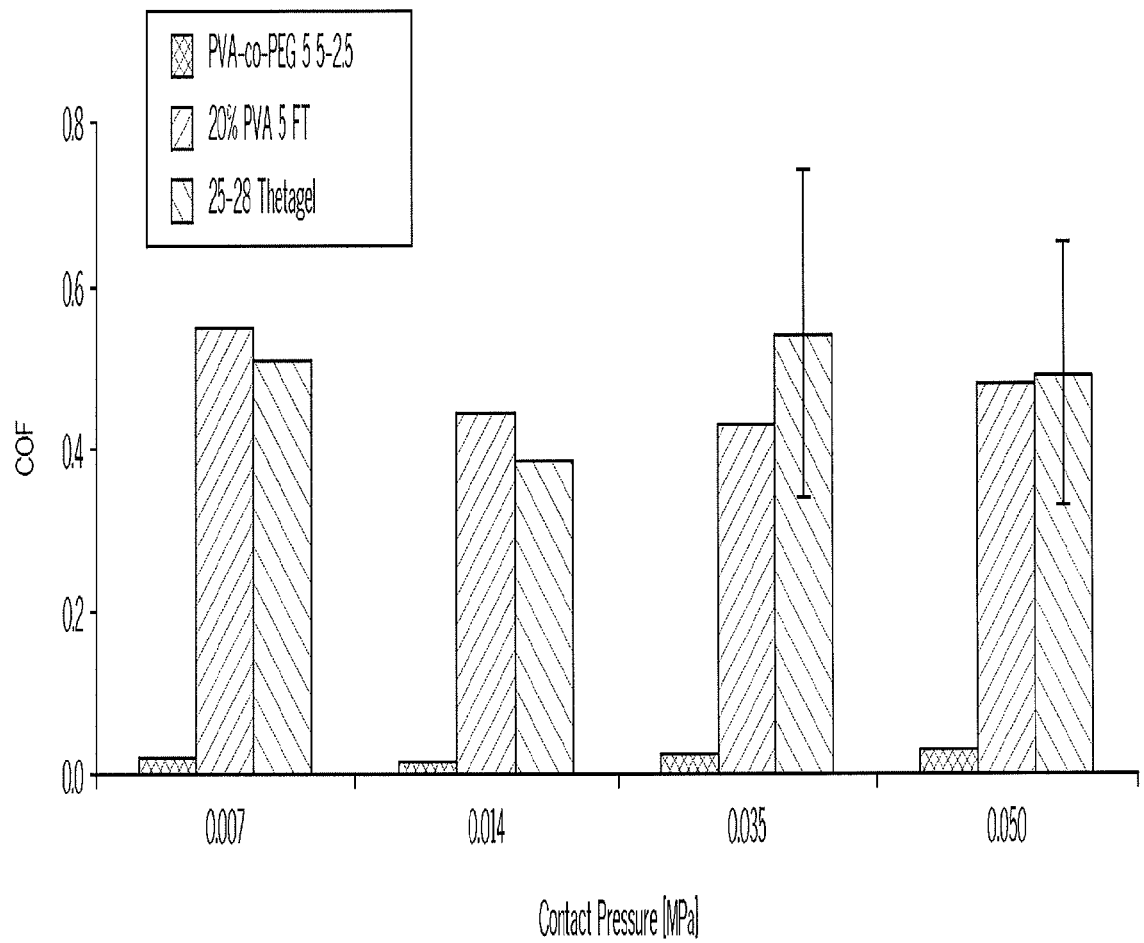
FIG. 7 illustrates coefficients of friction (COF) at four different contact pressures for the PVA-co-PEG 5-2.5 (5 wt % PEG-DMA and 2.5 wt % PEG-MeMA) hydrogel formulation and also a freeze-thawed (20% PVA 5 FT) PVA hydrogel and a PVA Thetagel. The tests were run in deionized water at 40° C.

Coefficient of friction (COF) tests were performed on a TA Instruments AR-1000 rheometer using a cobalt-chrome ring rotating against a flat hydrogel sample, following a procedure pioneered by Kavehpour and McKinley (Kavehpour, H. P.; McKinley, G. H. *Tribology Letters* 2004, 17, (2), 327-335). Tests were run in deionized water at 40° C. The COF values were calculated by averaging the torque at four predetermined normal force settings (1, 3, 5, and 7 N). The ring geometry guarantees that the sliding velocity is effectively constant everywhere in the test fixture. The normal force values were converted to contact pressures by dividing by the contact area of the ring. The coefficient of friction values are plotted in. FIG. 7 demonstrates coefficients of friction (COF) at four different contact pressures for the PVA-co-PEG 5-2.5 hydrogel (5 wt % PEG-DMA and 2.5 wt % PEG-MeMA) formulation and also a freeze-thawed (20% PVA 5 FT) PVA hydrogel and a PVA Thetagel.

Both the freeze-thawed and Thetagel samples had similarly high coefficients of friction which averaged approximately 0.5. The PVA-co-PEG 5-2.5 (5 wt % PEG-DMA and 2.5 wt % PEG-MeMA) sample, however, exhibited COF values of approximately 0.02, more than an order of magnitude lower than either of the physically-crosslinked PVA-based hydrogels. For comparison, reported values for the coefficient of friction of cartilage-on-cartilage are typically around 0.01 (see Mow, V. C.; Ratcliff, A., Poole, A. R. *Biomaterials* 1992, 13, (2), 67-97). Thus, PVA-co-PEG 5-2.5 (5 wt % PEG-DMA and 2.5 wt % PEG-MeMA) formulation exhibits a coefficient of friction comparable to cartilage-on-cartilage, even in a non-ideal medium such as saline, which has very different rheological properties from the joint fluid (see FIG. 7).

Example 3

Preparation of "Cryogel" Poly(Vinyl Alcohol) Hydrogel

A 15 wt % solution of poly(vinyl alcohol) (99+% hydrolyzed, Sigma-Aldrich cat. no. 363065) in distilled water was prepared by dispersing the polymer powder in water with stirring. While continuing to stir, the water was gradually warmed to ~90° C. and held at that temperature until the polymer was completely dissolved. The polymer solution was converted to a cryogel by alternatively freezing the solution at −20° C. for 16 hr and then thawing to room temperature, ~22° C. The freeze-thaw cycle was repeated 5 times. This procedure allows formation of associations of poly(vinyl alcohol) polymer chains which function as physical crosslinks and results in a poly(vinyl alcohol) cryogel.

Example 4

Preparation of Poly(Vinyl Acetate) Copolymer with Polyethylene Glycol Dimethacrylate A crosslinked copolymer hydrogel precursor of the current invention using polyethylene glycol dimethacrylate as crosslinking monomer was prepared as follows. Vinyl acetate (92.50 g, Sigma-Aldrich cat. no. V1503), polyethylene glycol dimethacrylate (5.00 g, Sigma-Aldrich cat. no. 409510), and polyethylene glycol methyl ether methacrylate (2.50 g, Sigma-Aldrich cat. no. 4479943) were weighed into a clean glass jar. 0.500 g azobisisobutyronitrile (Sigma-Aldrich cat. no. 441090) was added to the monomer mixture and dissolved with stirring for approximately 15 min. Approximately 7.4 g of the monomer/initiator solution was added to a 60 ml wide mouth PTFE jar. The head space in the jar was replaced with argon gas, and the jar sealed. The sealed jar was placed in a 40° C. oven for 7 days. The polymerized crosslinked poly(vinyl acetate-co-polyethylene glycol methyl ether methacrylate) copolymer is a hazy tough material. The cast copolymer is about 45 mm in diameter and 4-5 mm thick.

Example 5

Deacetylation of Poly(Vinyl Acetate) Copolymer Crosslinked with Polyethylene Glycol Dimethacrylate and Gel Hydration The cast copolymer of Example 4 was converted to a hydrogel using the following procedure. The cast copolymer was placed in a 400 ml wide mouth jar in about 95 ml of anhydrous methanol and gently swirled for 16 hr. During this time the copolymer absorbed methanol and swelled to about 71 mm in diameter. Five ml of 30% (wt/vol) potassium hydroxide/methanol solution was added to the jar, and the gentle swirling continued. After 8 hrs in the potassium hydroxide/methanol solution the copolymer was white opaque and less swollen than in the pure methanol. The alkaline methanol was decanted, and 200 ml distilled water added to the jar and copolymer. The copolymer was again gently swirled for 16 hr. The distilled water was then replaced with 200 ml of fresh distilled water and the swirling continued for an additional 24 hr. The pH of the water was tested and found to be neutral. The distilled water was again exchanged for 200 ml of fresh distilled water. The copolymer hydrogel is a hazy colorless swollen gel with an extremely lubricious surface. The equilibrium water content of the gel is about 69 wt %.

Example 6

Preparation of Poly(Vinyl Acetate) Copolymer with Diallyl Succinate

A crosslinked copolymer hydrogel precursor of the current invention using diallyl succinate as crosslinking monomer was prepared as follows. Vinyl acetate (92.50 g, Sigma-Aldrich cat. no. V1503), diallyl succinate (2.50 g, Sigma-Aldrich cat. no. 105333), polyethylene glycol methyl ether methacrylate (5.00 g, Sigma-Aldrich cat. no. 4479943), and tert-butanol (25.00 g, Sigma-Aldrich cat. no. 24127) were weighed into a clean glass jar. 0.500 g 2,2'-azobis(2,4-dimethylvaleronitrile) (Wako Chemical V-65) was added to the monomer mixture and dissolved with stirring for approximately 15 min. Approximately 7.4 g of the monomer/initiator solution was added to a 60 ml wide mouth PTFE jar. The head space in the jar was replaced with argon gas, and the jar sealed. The sealed jar was placed in a 40° C. oven for 16 hrs. The polymerized crosslinked poly(vinyl acetate-co-polyethylene glycol methyl ether methacrylate) copolymer is a transparent tough material. The cast copolymer is about 45 mm in diameter and 4-5 mm thick.

Example 7

Deacetylation of Poly(Vinyl Acetate) Copolymer Crosslinked with Diallyl Succinate and Gel Hydration The cast copolymer of Example 6 was converted to a hydrogel using the procedures described in Example 5. The copolymer hydrogel crosslinked with diallyl succinate is a transparent swollen gel with an extremely lubricious surface. The equilibrium water content of the gel is about 67 wt %.

Examples 8-9

Preparation of Additional Poly(Vinyl Acetate) Copolymer Hydrogels with 2.50 pph Diallyl Succinate Additional copolymer hydrogels were prepared varying the amount of vinyl acetate and polyethylene glycol methyl ether methacrylate monomers. The polymerization, deacetylation and hydration procedures describe in Examples 6 and 7 were used. The hydrogel prepared from a 95.0 vinyl acetate-2.5 diallyl succinate-2.5 polyethylene glycol methyl ether methacrylate solution has an equilibrium water content of about 59 wt %. The hydrogel prepared from a 87.5 vinyl acetate-2.5 diallyl succinate-10.0 polyethylene glycol methyl ether methacrylate solution has an equilibrium water content of about 83 wt %.

Example 10

Measurement of Dynamic Coefficient of Friction of Hydrogels

Dynamic coefficient of friction was determined on hydrogel samples using the following procedure. A TA Instruments AR-1000 Rheometer (TA Data Analysis software) equipped with a 31.8 mm diameter cobalt-chromium thin ring coefficient of friction rheometer fixture and constant temperature distilled water sample pan was used. The sample pan was modified by adhering a fine grit emory cloth to the bottom of the pan. This was done to prevent slippage of the hydrogel sample during test. After total system inertia is calibrated and the zero point of the rheometer ring fixture is set, the hydrogel test piece was placed in the sample pan and the distilled water bath brought up to 40° C. The AR-1000 directly measures the torque required to rotate the cobalt-chromium ring in contact with the hydrogel sample at several values of normal force. In order to find coefficient of friction, $\mu$, from the torque and normal force data, a relationship between torque (T) and shear stress ($\tau$) is needed. Using equations (1) and (2) below, and assuming that when $(R_2-R_1)/R_1 \ll 1$, the shear stress will vary linearly around an average shear stress $\tau_{\bar{R}}$ such that $\tau(r)=r/\bar{R})\tau_{\bar{R}}$, the desired relationship can be found as shown in equation (3), where $\bar{R}$ is the average of $R_1$ and $R_2$.

$$F_s = \int_A \tau dA \tag{1}$$

$$T = \int_{R_1}^{R_2} \int_0^{2\pi} r\tau(r) rd\theta dr \tag{2}$$

$$\tau_R = \frac{2\bar{R}}{R_2^4 - R_1^4} T \tag{3}$$

Using equation (4) for normal stress and the definition for coefficient of friction found in equation (5), the coefficient of friction can be calculated using values which are either known or measured during each test (equation (6)).

$$\sigma_N = \frac{F_N}{\pi(R_2^2 - R_1^2)} \tag{4}$$

$$\mu = \frac{\tau_R}{\sigma_N} \tag{5}$$

$$\mu = \left(\frac{R_2 + R_1}{R_2^2 + R_1^2}\right)\left(\frac{T}{F_N}\right) \tag{6}$$

Normal force [N] and coefficient of friction determinations for the hydrogel materials prepared in the above examples are shown in Table 3.

TABLE 3

Examples of coefficient of friction data.

Example 3 hydrogel - 15% PVA 5 F/T Gel

| | | | | | |
|---|---|---|---|---|---|
| N | 1.35 | 3.91 | 5.88 | 6.91 | 8.90 |
| μ | 0.517 | 0.349 | 0.342 | 0.353 | 0.373 |

Example 5 hydrogel - 5PEGDMA 2.5PEG-MeMA

| | | | | |
|---|---|---|---|---|
| N | 0.94 | 2.95 | 4.87 | 7.15 |
| μ | 0.093 | 0.112 | 0.179 | 0.232 |

Hydrogel - 2.5DAS 0PEG-MeMA

| | | | | |
|---|---|---|---|---|
| N | 1.04 | 2.90 | 5.02 | 6.96 |
| μ | 0.075 | 0.059 | 0.059 | 0.063 |

Example 7 hydrogel - 2.5DAS 5PEG-MeMA

| | | | | |
|---|---|---|---|---|
| N | 1.00 | 2.51 | 4.52 | 6.54 |
| μ | 0.012 | 0.014 | 0.022 | 0.030 |

Example 8 hydrogel - 2.5DAS 2.5PEG-MeMA

| | | | | |
|---|---|---|---|---|
| N | 0.94 | 2.88 | 4.83 | 6.77 |
| μ | 0.045 | 0.032 | 0.039 | 0.055 |

Example 9 hydrogel - 2.5DAS 10PEG-MeMA

| | | | |
|---|---|---|---|
| N | 0.79 | 1.73 | 3.42 |
| μ | 0.055 | 0.036 | 0.029 |

It is to be understood that the description, specific examples and data, while indicating exemplary embodiments, are given by way of illustration and are not intended to limit the present invention. Various changes and modifications within the present invention will become apparent to the skilled artisan from the discussion, disclosure and data contained herein, and thus are considered part of the invention.

What is claimed is:

1. A method of making a hydrolyzed cross-linked polyvinyl alcohol (PVA)—hydrogel, wherein the method comprises the steps of:
   (a) polymerizing vinyl acetate (VAc) monomers in the presence of a crosslinking agent having two or more end groups comprised of methacrylate groups wherein the methacrylate groups comprise acrylate or any end group having two double bonds that are compatible with the vinyl acetate and one or more monofunctional monomer molecules, thereby producing a crosslinked poly(vinyl acetate) (PVAc) polymer network containing pendant chains;
   (b) hydrolyzing the crosslinked PVAc polymer network, thereby forming a hydrogel having a crosslinked hydrophilic PVAc polymer network; and
   (c) hydrating the PVAc polymer network, thereby forming a hydrolyzed cross-linked hydrogel having a hydrophilic PVAc polymer network and pendant chains.

2. The method of claim 1, wherein the cross-linking agent is ethyleneglycol dimethacrylate (EG-DMA), diallyl succinate, polyethylene glycol divinyl ether, or butanediol diacrylate.

3. The method of claim 1, wherein the crosslinking agent is PEG-DMA.

4. The method of claim 1, wherein the crosslinking agent is dimethacrylate with one or more lactic acid groups.

5. The method of claim 1, wherein the crosslinking agent is dimethacrylate with one or more HEMA groups.

6. The method of claim 1, wherein the hydrolysis is carried out in a basic alcohol solution.

7. The method of claim 6, wherein the basic alcohol solution is methanol and KOH.

8. The method of claim 7, wherein the methanol is added first and allowed to swell the polymer network completely or partially before addition of the KOH.

9. The method of claim 1, wherein the monofunctional monomeric molecule is PEG-MeMA.

10. The method of claim 1, wherein the monofunctional monomeric molecule is mono-methacrylate with one or more lactic acid groups.

11. The method of claim 1, further comprising an ingredient that does not polymerize.

12. The method of claim 1, wherein the hydrolysis is carried out in a solution containing a blend of solvents having at least one solvent that has an affinity for the first crosslinked polymer network and at least one solvent with an affinity for the hydrolyzed polymer network.

13. The method of claim 1, wherein a mold is used to control the shape of the polymer network.

14. The method of claim 1, wherein the crosslinked network surface is exposed to further mono-functional molecules and polymerized to modify the surface relative to the bulk.

15. The method of claim 1, wherein the monomer is polymerized into a porous material.

16. A hydrolyzed cross-linked polyvinyl alcohol (PVA)-hydrogel made by a method comprising the steps of:
   (a) polymerizing vinyl acetate (VAc) monomers in the presence of a crosslinking agent having two or more end groups comprised of methacrylate groups wherein the methacrylate groups comprised acrylate or any end group having two double bonds that are compatible with vinyl acetate and one or more monofunctional monomer molecules, thereby producing a crosslinked poly(vinyl acetate) (PVAc) polymer network containing pendant chains;
   (b) hydrolyzing the crosslinked PVAc polymer network, thereby forming a hydrogel having a crosslinked hydrophilic PVAc polymer network; and
   (c) hydrating the PVAc polymer network, thereby forming a hydrolyzed cross-linked hydrogel having a hydrophilic PVAc polymer network and pendant chains.

17. The hydrolyzed cross-linked polyvinyl alcohol (PVA)-hydrogel of claim 16, wherein the hydrophilic polymer network is implanted in a human body.

18. The hydrolyzed cross-linked polyvinyl alcohol (PVA)-hydrogel of claim 16, wherein the hydrophilic polymer network is a thread or filament.

* * * * *